(12) United States Patent
Voorhees

(10) Patent No.: US 8,294,014 B2
(45) Date of Patent: Oct. 23, 2012

(54) PORTABLE STAND AND MOUNT FOR SECURING A PORTABLE MEDIA OR AUDIO PLAYER TO A SUPPORT

(76) Inventor: Jeffry Voorhees, Burbank, CA (US)

( * ) Notice: Subject to any disclaimer, the term of this patent is extended or adjusted under 35 U.S.C. 154(b) by 39 days.

(21) Appl. No.: 12/855,665

(22) Filed: Aug. 12, 2010

(65) Prior Publication Data

US 2011/0192269 A1    Aug. 11, 2011

Related U.S. Application Data

(60) Provisional application No. 61/233,814, filed on Aug. 13, 2009.

(51) Int. Cl.
*G10D 3/00* (2006.01)

(52) U.S. Cl. .................. 84/453; 84/327; 84/329; 84/421

(58) Field of Classification Search .................... 84/453, 84/327, 329, 421
See application file for complete search history.

(56) References Cited

U.S. PATENT DOCUMENTS

| | | | | |
|---|---|---|---|---|
| 432,305 | A * | 7/1890 | Foley | 248/229.26 |
| 1,320,439 | A * | 11/1919 | Tavi | 248/447.2 |
| 1,907,238 | A * | 5/1933 | Blondin | 84/327 |
| 3,550,495 | A * | 12/1970 | Shotmeyer | 84/267 |
| D261,703 | S * | 11/1981 | Plummer | D6/449 |
| D276,779 | S * | 12/1984 | Gomez | D6/418 |
| 4,531,443 | A * | 7/1985 | Gillis, Jr. | 84/329 |
| 4,606,525 | A * | 8/1986 | Lombardi | 248/460 |
| D286,478 | S * | 11/1986 | Oakes, Jr. | D6/419 |
| 4,984,760 | A * | 1/1991 | Cohn et al. | 248/126 |
| 5,154,380 | A * | 10/1992 | Risca | 248/154 |
| 5,187,744 | A * | 2/1993 | Richter | 379/449 |
| 5,522,300 | A * | 6/1996 | Cheatwood | 84/453 |
| 5,839,919 | A * | 11/1998 | Chen | 439/529 |
| 5,845,885 | A * | 12/1998 | Carnevali | 248/181.1 |
| 5,853,158 | A * | 12/1998 | Riggle | 248/311.2 |
| 6,158,793 | A * | 12/2000 | Castro | 296/1.07 |
| 6,255,569 | B1 * | 7/2001 | Ward | 84/329 |
| 6,797,872 | B1 * | 9/2004 | Catalano et al. | 84/454 |
| 6,802,484 | B1 * | 10/2004 | Kiley et al. | 248/311.2 |
| 6,892,994 | B1 * | 5/2005 | Renshaw | 248/346.04 |
| D510,205 | S * | 10/2005 | Nickel | D6/418 |
| 7,040,590 | B2 * | 5/2006 | Carnevali | 248/311.2 |
| 7,265,282 | B2 * | 9/2007 | Membreno et al. | 84/453 |
| 7,320,450 | B2 * | 1/2008 | Carnevali | 248/160 |
| 7,403,613 | B2 * | 7/2008 | Liou | 379/455 |
| 7,458,555 | B2 * | 12/2008 | Mastropaolo et al. | 248/447.2 |
| 7,515,709 | B2 * | 4/2009 | Richter | 379/446 |
| 7,551,458 | B2 * | 6/2009 | Carnevali | 361/807 |
| 7,732,692 | B2 * | 6/2010 | Mori et al. | 84/421 |
| D619,559 | S * | 7/2010 | Voorhees | D14/203.6 |
| D625,715 | S * | 10/2010 | Adams, II | D14/253 |
| 7,925,320 | B2 * | 4/2011 | Pemble et al. | 455/575.9 |
| 8,007,188 | B2 * | 8/2011 | Orf | 396/419 |
| 8,020,829 | B1 * | 9/2011 | Tamayori | 248/447.2 |
| D646,315 | S * | 10/2011 | Orf | D16/242 |
| D647,917 | S * | 11/2011 | Voorhees | D14/496 |
| D652,045 | S * | 1/2012 | Hong | D14/447 |
| D652,836 | S * | 1/2012 | Voorhees | D14/447 |
| D660,306 | S * | 5/2012 | Voorhees | D14/447 |

(Continued)

*Primary Examiner* — David Warren
*Assistant Examiner* — Robert W Horn
(74) *Attorney, Agent, or Firm* — Buche & Associates, P.C.; John K Buche

(57) ABSTRACT

Disclosed is an apparatus for securing a media or audio player to a support and the related methods of use.

17 Claims, 14 Drawing Sheets

U.S. PATENT DOCUMENTS

| | | | |
|---|---|---|---|
| 2005/0098692 A1* | 5/2005 | Yang | 248/163.1 |
| 2007/0221694 A1* | 9/2007 | Aguiliar et al. | 224/420 |
| 2008/0061195 A1* | 3/2008 | Carnevali | 248/125.8 |
| 2008/0061210 A1* | 3/2008 | Carnevali | 248/447 |
| 2008/0163739 A1* | 7/2008 | Mori | 84/421 |
| 2008/0203260 A1* | 8/2008 | Carnevali | 248/316.5 |
| 2009/0000457 A1* | 1/2009 | Dunlop | 84/329 |
| 2009/0060473 A1* | 3/2009 | Kohte et al. | 386/124 |
| 2010/0067729 A1* | 3/2010 | Upham et al. | 381/363 |
| 2011/0192269 A1* | 8/2011 | Voorhees | 84/421 |
| 2011/0255226 A1* | 10/2011 | Duncan Seil et al. | 361/679.01 |
| 2011/0283863 A1* | 11/2011 | Dunlop | 84/329 |

* cited by examiner

PORTABLE STAND AND MOUNT FOR SECURING A PORTABLE MEDIA OR AUDIO PLAYER TO A SUPPORT

CROSS-REFERENCE TO RELATED APPLICATIONS

This application claims the priority of U.S. Prov. Pat. App. Ser. No. 61/233,814 (filed Aug. 13, 2009) entitled "A PORTABLE STAND AND MOUNT FOR SECURING A PORTABLE MEDIA OR AUDIO PLAYER TO A SUPPORT."

STATEMENT REGARDING FEDERALLY SPONSORED RESEARCH OR DEVELOPMENT

Not applicable.

BACKGROUND OF THE INVENTION

1. Field of Invention

This invention is in the field of an apparatus for securing a portable media or audio player to a drum kit or other musical instrument or a support.

2. Background of the Invention

Various types and sizes of media or audio players are available for use by a musical instrument playing musician. Frequently, musicians, especially drummers, use the media/audio players to produce accompaniment for practicing or performing the operation of their chosen musical instrument. Accordingly, the musician must change, from time-to-time, between operation of the media/audio player and the musical instrument.

Under such circumstances, conventional use and operation methods for the media or audio players have typically been inadequate. Typically, the musician cannot always have the musical instrument and the media/audio player within operable reach, thereby increasing the down-time associated with operating the media/audio player. Furthermore, the typical location for the musician to place the media/audio player is not readily adaptable to media/audio players of differing sizes and shapes.

SUMMARY OF THE INVENTION

Accordingly, it is an object of the present invention to provide an apparatus and the associated methods for placing a media and audio player within the operable reach of a musician playing a musical instrument, possibly even on the instrument itself.

It is an object of the present invention to provided an apparatus and the associated methods for providing a location wherein media/audio players of different physical dimensions and shapes may be placed.

It is an object of the present invention to provided an apparatus and the associated methods for facilitating the media/audio player accompaniment of a musician playing a musical instrument.

It is yet another object of the present invention to provided an apparatus adjustable to accommodate different devices and positions as well as rapid placement and removal.

BRIEF DESCRIPTION OF THE FIGURES

Other objectives of the invention will become apparent to those skilled in the art once the invention has been shown and described. The manner in which these objectives and other desirable characteristics can be obtained is explained in the following description and attached figures.

It is to be noted, however, that the appended figures illustrate only typical embodiments of this invention and are therefore not to be considered limiting of its scope, for the invention may admit to other equally effective embodiments that will be appreciated by those reasonably skilled in the relevant arts. Also, figures are not necessarily made to scale but are representative.

DETAILED DESCRIPTION OF PREFERRED EMBODIMENTS

In general, the apparatus 1 of the present invention defines a means for placing different sized and shaped media/audio players within the operable reach of a musician playing a musical instrument. In general operation, the apparatus 1 may: be removably attached to a support and positioned within the operable reach of a musician; be customized to the size and/or shape of a media/audio player; and, receive a media/audio player.

Figure 1:
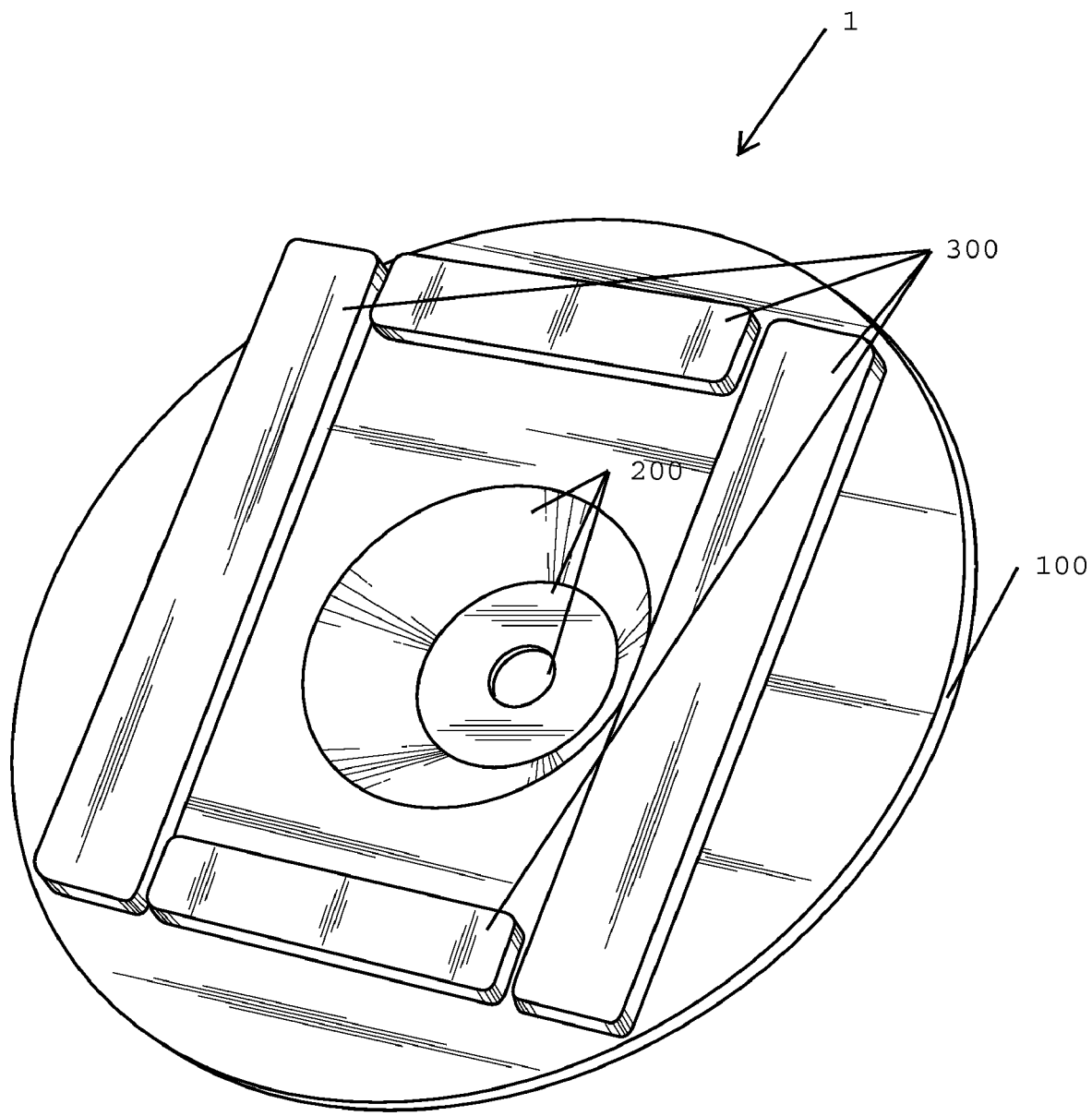
FIG. 1 is an overhead perspective view of the apparatus 1 of the present application.

FIG. 1 illustrates an overhead perspective view of the apparatus 1 of the present invention. As seen in the figure, the apparatus 1 typically comprises three main features: (1) a support platform 100; (2) a base 200; and (3) a means for securing a particular media/audio player 300 to the apparatus 1.

Figure 2:
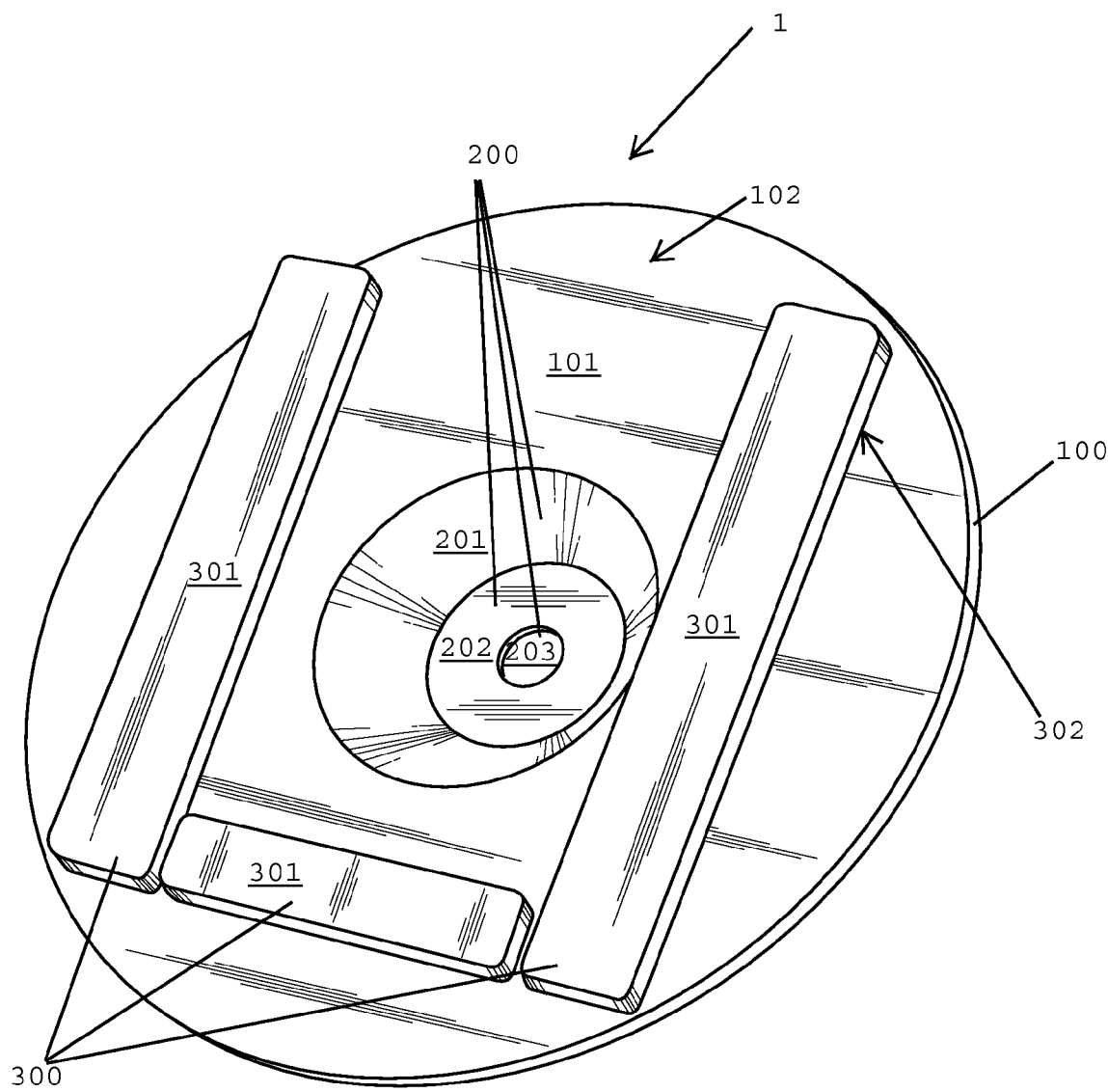
FIG. 2 is an overhead perspective view of another configuration of the apparatus 1 of the present invention.

FIG. 2 also illustrates an overhead perspective view of the apparatus 1, but, unlike FIG. 1, FIG. 2 illustrates the securing means 300 in one of many different configurations.

Figure 3:
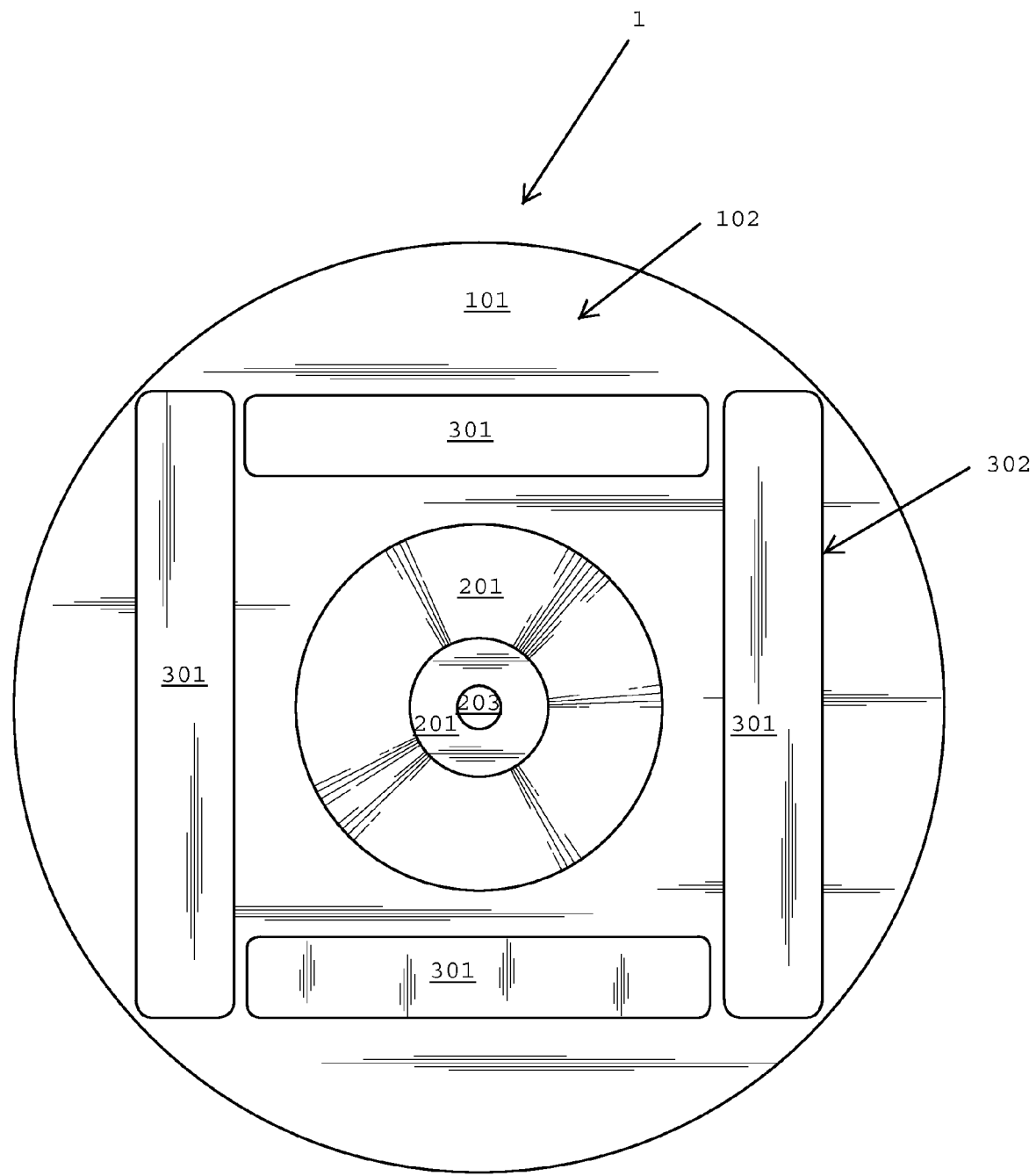
FIG. 3 is a top view of the apparatus 1 depicted in FIG. 1.
Figure 4:
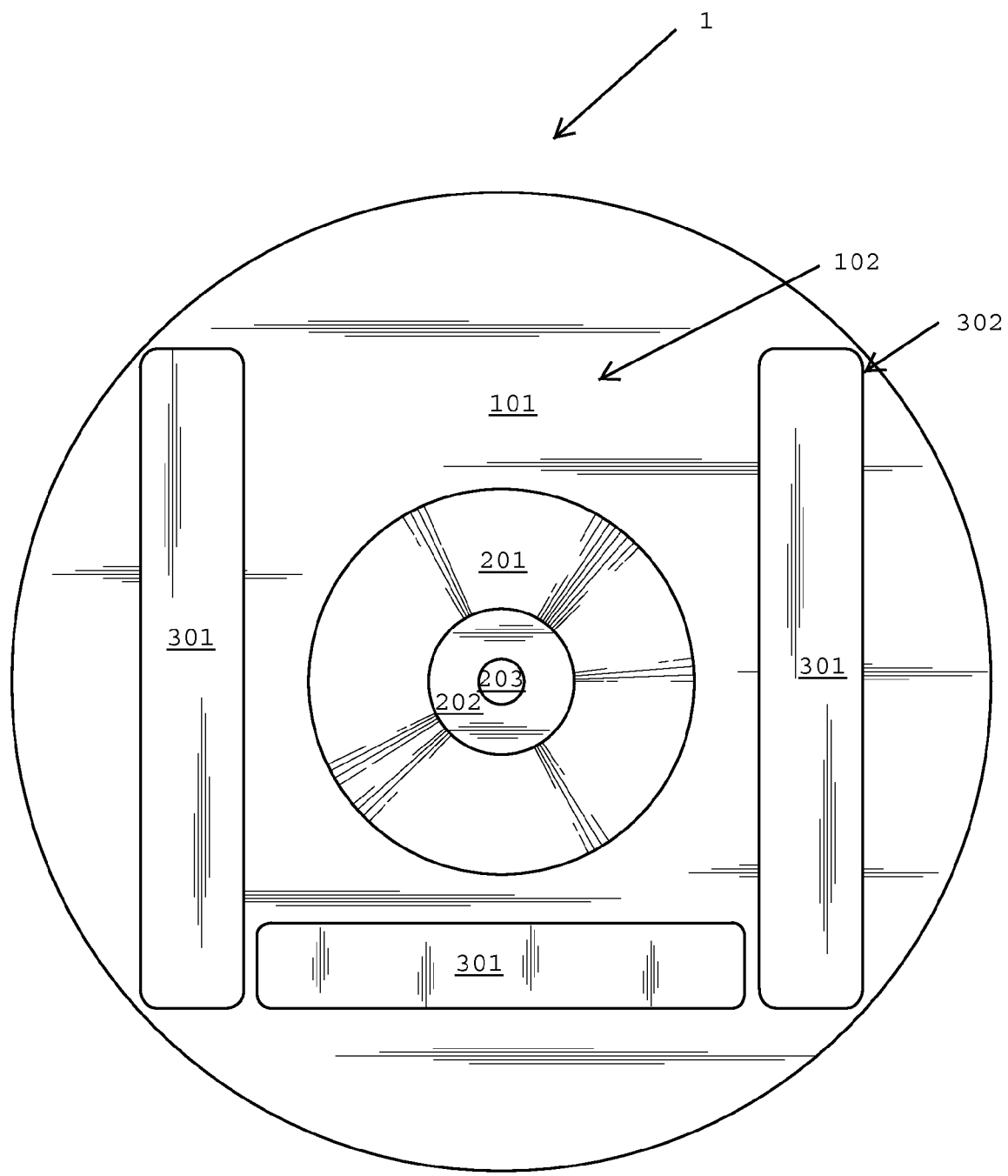
FIG. 4 is a top view of the apparatus 1 depicted in FIG. 2.

FIGS. 3 and 4 respectively depict a top view of the apparatus 1 in the FIG. 1 and FIG. 2 configurations. FIGS. 3 and 4 also depict the preferable structure of the support platform 100. Still referring to FIGS. 3 and 4, the support platform 100 may be defined by a surface 101 planarly extending around the top of the base 200. Preferably, the surface 101 features an adhering means 102 for removably and repeatably associating the surface 101 with the securing means 300 (compare FIG. 3 with FIG. 4 wherein a portion of the securing means 300 has been detached from the surface 101 of the apparatus 1 to create a different securing means 300 configuration). However, as discussed below, a cooperating adhering means 302 may also be provided to the securing means 300. In the preferable embodiment, the cooperating adhering means 102 and 302 may be a hook and loop fastener system, as has been marketed under Velcro® trademarks or some other adhesive for repeatable attachment/removal.

Figure 5:
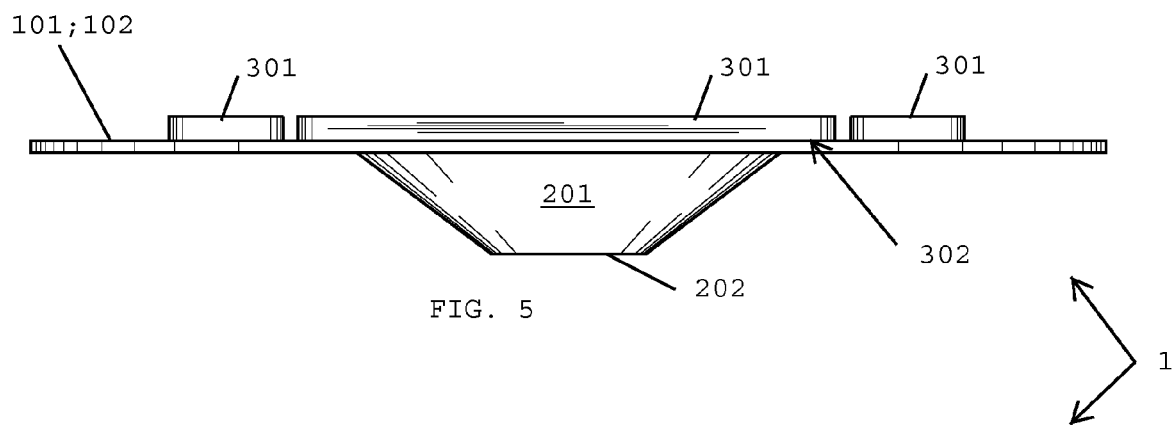
FIG. 5 is a side view of the apparatus 1 depicted in FIGS. 1 and 3.
Figure 6:
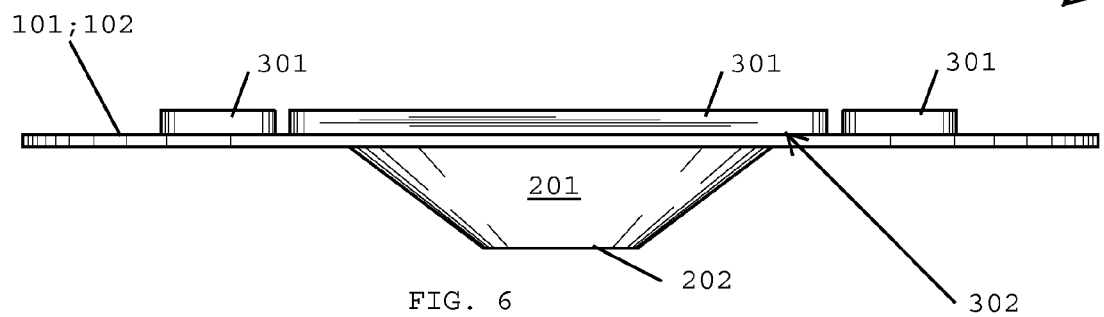
FIG. 6 is a side view of the apparatus 1 depicted in FIGS. 2 and 4.

FIGS. 5 and 6 respectively depict a side view of the apparatus 1 in the FIG. 1 and FIG. 2 configurations. FIGS. 3 through 6 also depict the preferable structure of the base 200. Still referring to FIG. 3 through 6, the base 200 is preferably defined by a connecting wall 201, a bottom 202, and an aperture 203. In one embodiment, the base 200 may define a depression on the support platform 100 (i.e., the wall 201 merges into both the bottom 202 and the surface 101). In another embodiment, the base 200 may be a separate component from the surface 101 and (in such a case) adhesive, weld, fasteners (including male-female screw and nut insertion of the base 200 into the platform 100), and other fasting means known to one of skill in the art may be employed for assembling the base 200 and support platform 100. Finally, the aperture 203 may define a means for attaching the apparatus 1 to a support via a nut and bolt system, or the like, interacting therewith.

FIGS. 1 through 6 respectively illustrate two different configurations of the apparatus 1. More specifically, FIGS. 2, 4, and 6 depict the apparatus 1 wherein the securing means 300 has been adapted to a different configuration than depicted in FIGS. 1, 3, and 5. A comparison of the two depicted configurations, discloses information about the structure and function of the securing means 300.

FIGS. 1 and 2 best depict the preferable structure of the securing means 300. As seen in the stated figures, the securing means 300 is defined by a plurality of support structures 301. The specific dimensions of the support structures 301 may vary depending on the media/audio player to be supported. Subject thereto, the support structures are preferably between the thickness (i.e., distance protruding from the surface 101) of zero-point-one centimeters (0.1 cm) and four inches (4 in). It should be noted that the size of the securing means 300 may vary in size and shape in order to accommodate plugs and volume controls used with the media/audio player (see the photos appended to the drawings). As seen by comparing FIGS. 1 and 2, structures 301 composing the securing means 300 may be exchanged, depleted or supplemented with structures 301 of the same or varying dimensions (see also FIGS. 7 through 10). The support structures 301 may be made of foam, wood, rubber, plastic, metal, and etcetera. As discussed above support structures may preferably feature an adhering means 302 for cooperating with the adhering means 102 on the surface 101. In an alternate embodiment, the support structures 301 may feature an independent adhering means 302 or none at all. In the preferable embodiment, the adhering means 102 and 302 are a hook and loop fastener system, as has been marketed under Velcro® trademarks or some other adhesive for repeatable attachment/removal or some other adhesive for repeatable attachment/removal. In alternate embodiments of the securing means 300, the securing means 300 may feature a strap that extends over a media/audio player to retain it within the securing means.

FIGS. 3 and 4 best depict the preferable function of the securing means 300. As seen in the stated figures, the location of the support structures 301 may be manipulated about the surface 101 to fit the size and shape of the would-be supported media/audio player. Manipulation of the support structure 301 location may be accomplished via detaching the individual support structures 301 from the surface 101 (i.e., disengaging the adhering means 102 and 103) and subsequently refastening the structure 301 to a different spot on the surface 101. For example, a structure 301 from the apparatus 1 configuration of FIG. 3 may be removed to create the apparatus 1 configuration of FIG. 4 in order to accommodate a media/audio player of greater length.

Figure 7:
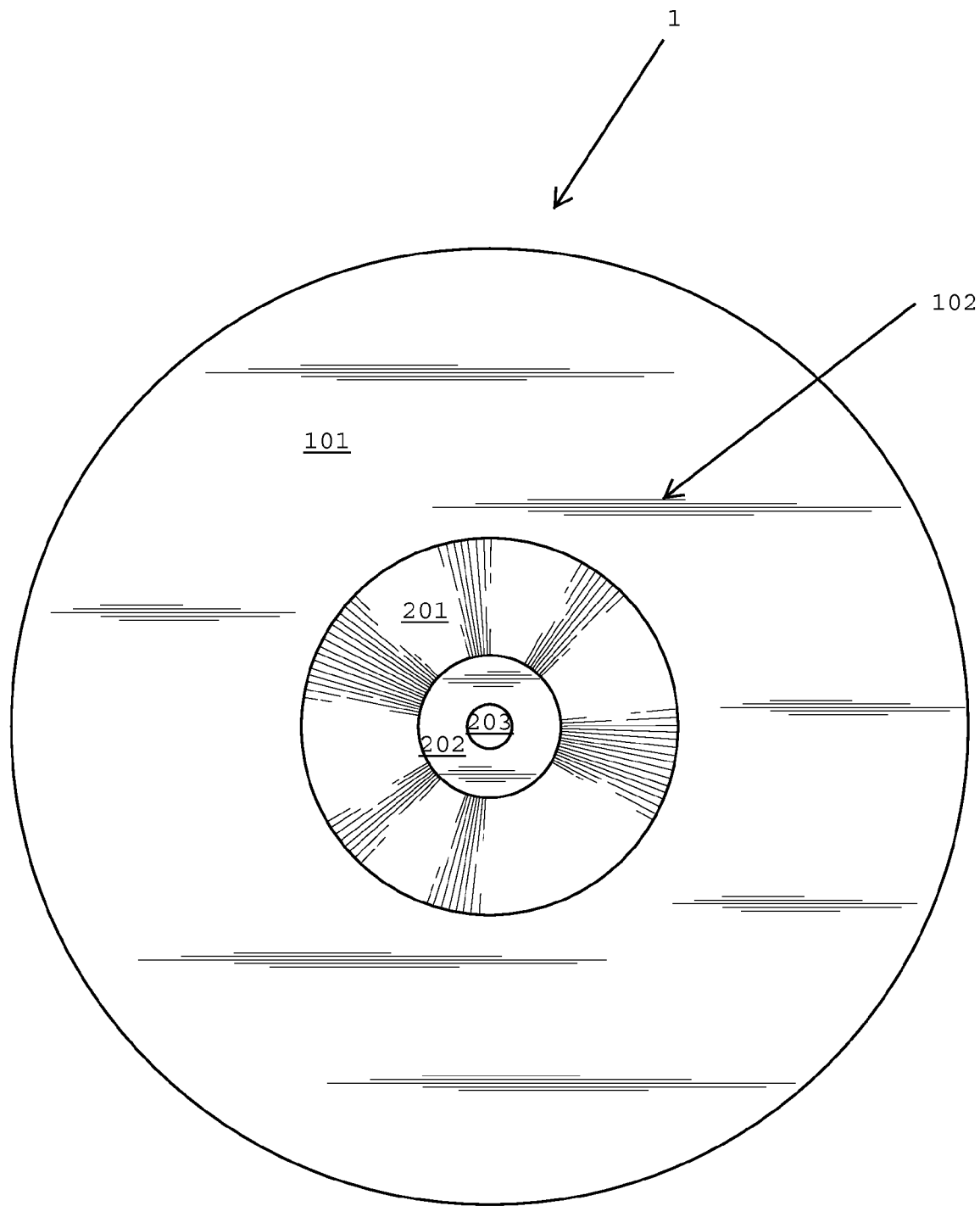
FIGS. 7, 8, 9, and 10 are top views of alternative configurations of the apparatus 1 of the present invention.
Figure 8:
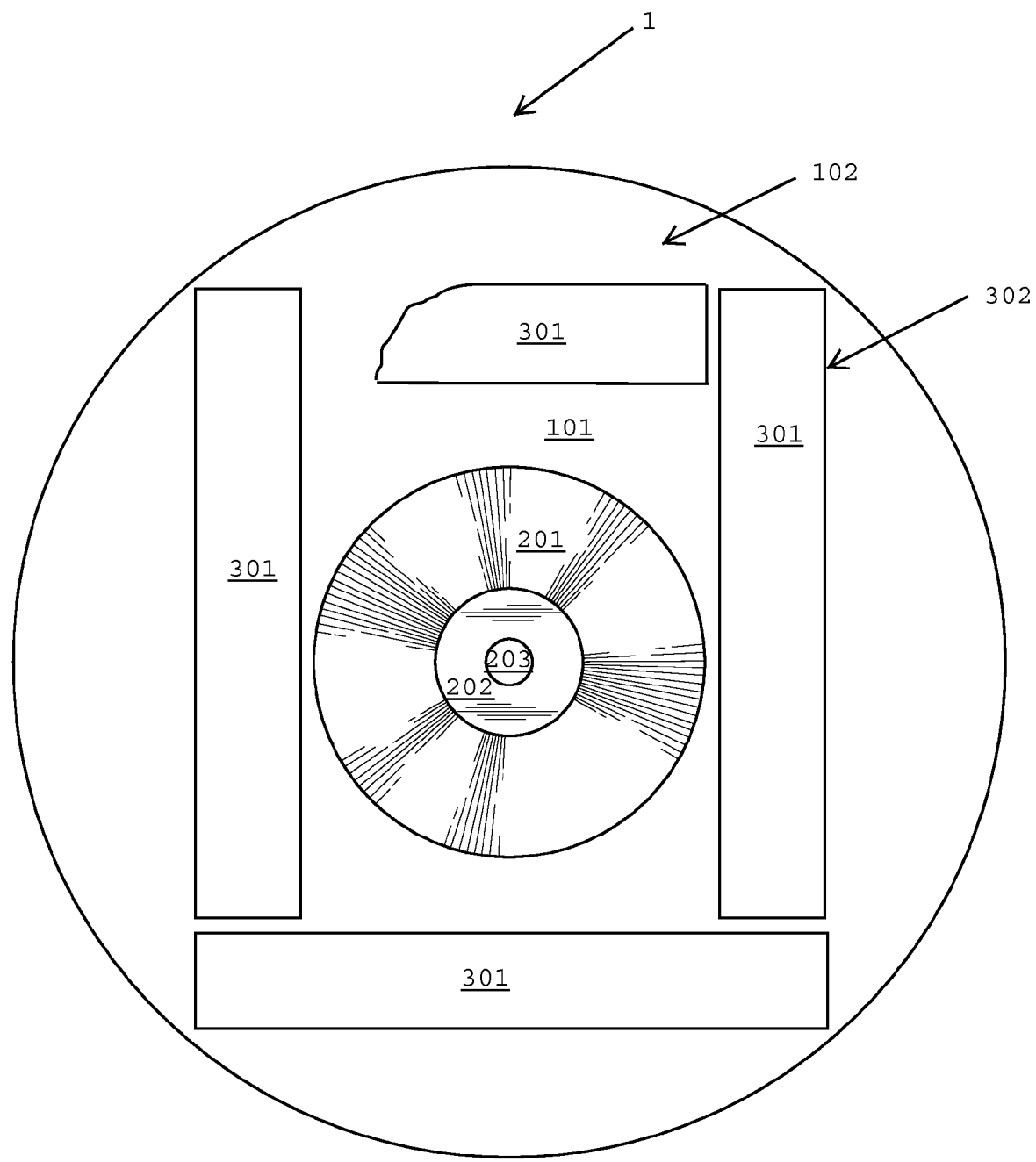
Figure 9:
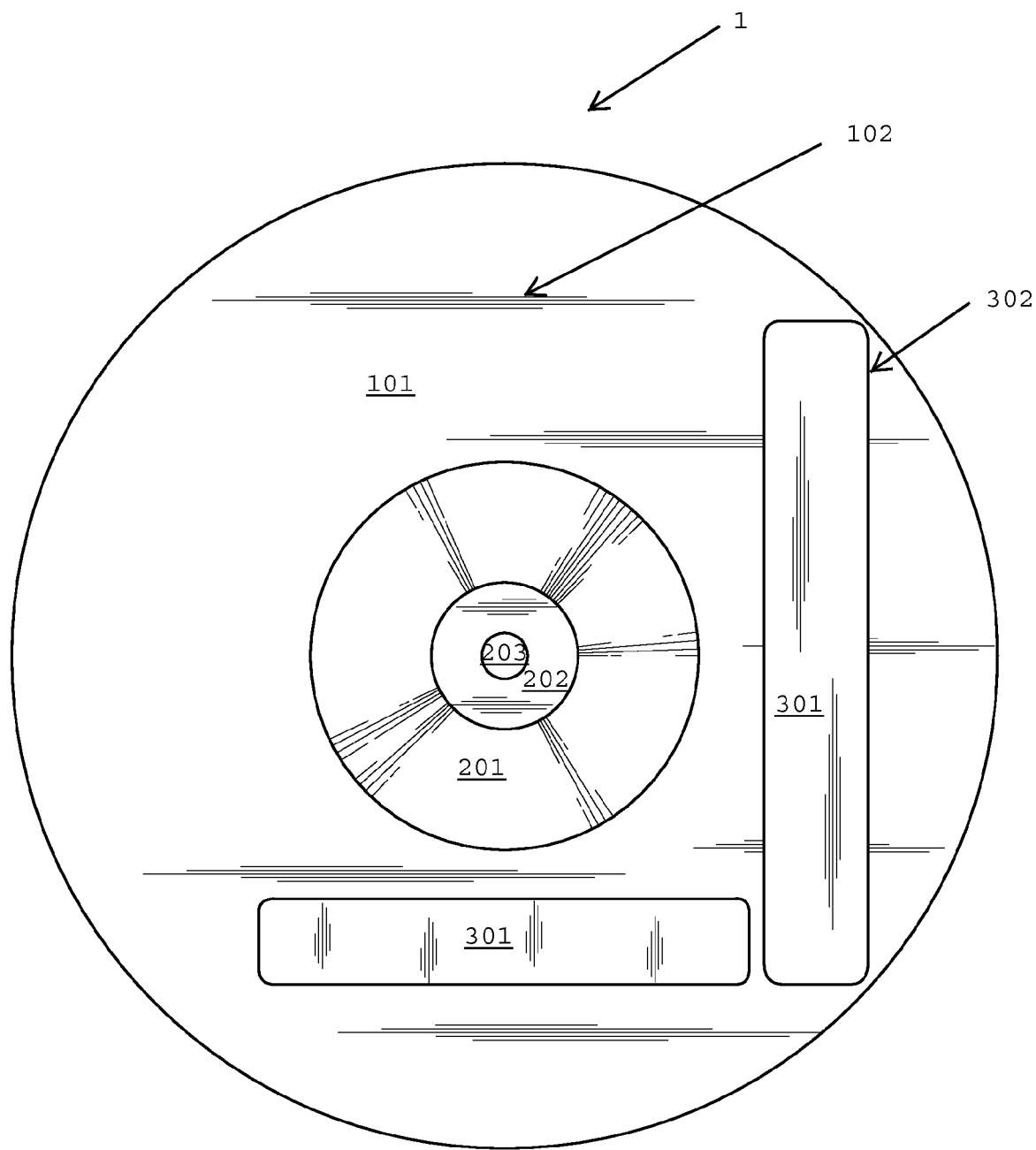
Figure 10:
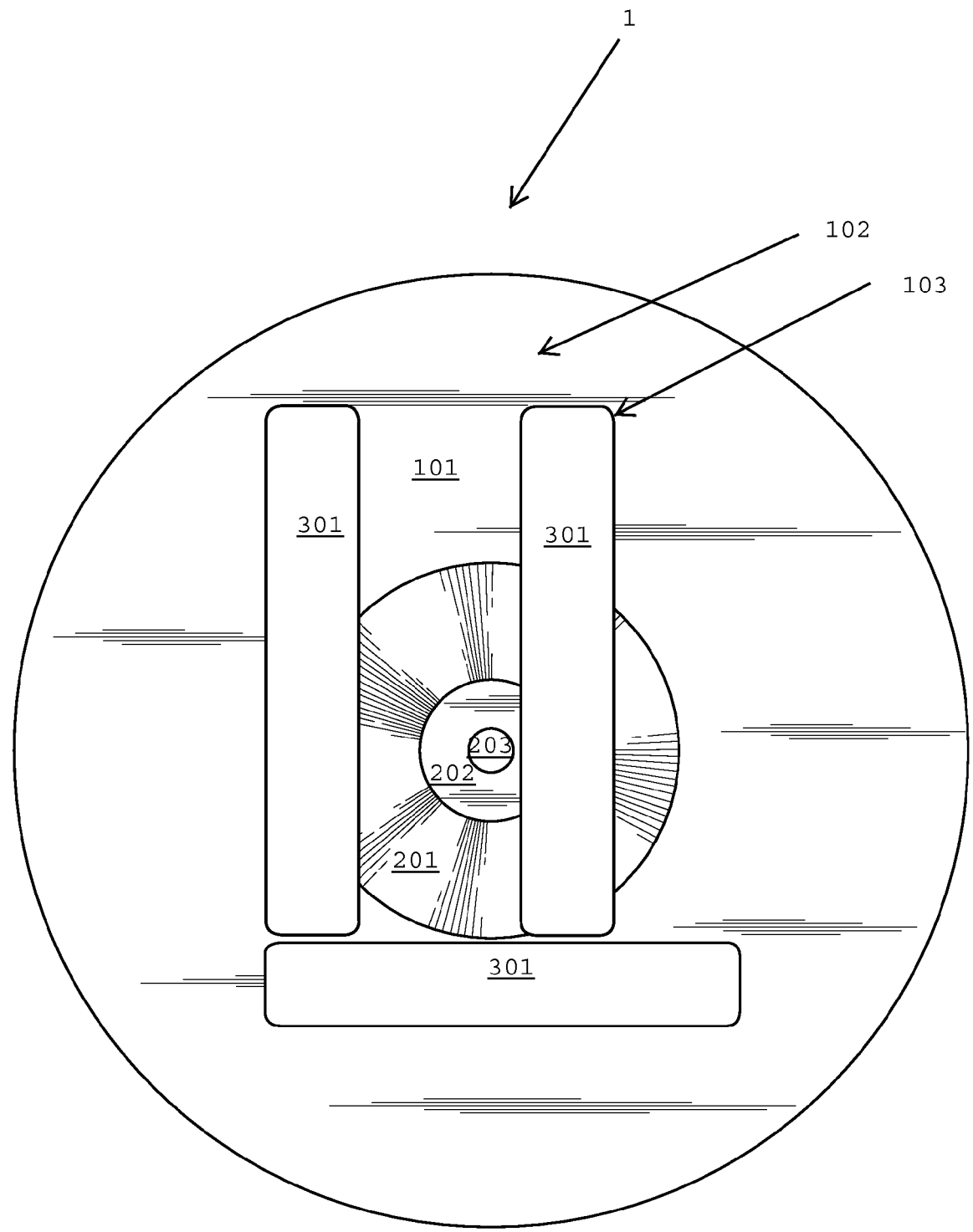

FIG. 7 illustrates the top view of the apparatus with the securing means 300 entirely removed for supporting a media/audio player that occupies the substantial portion of the surface 101. FIG. 8 through 10 illustrate variations and of the securing means 300 configuration on the apparatus 1.

Figure 11:
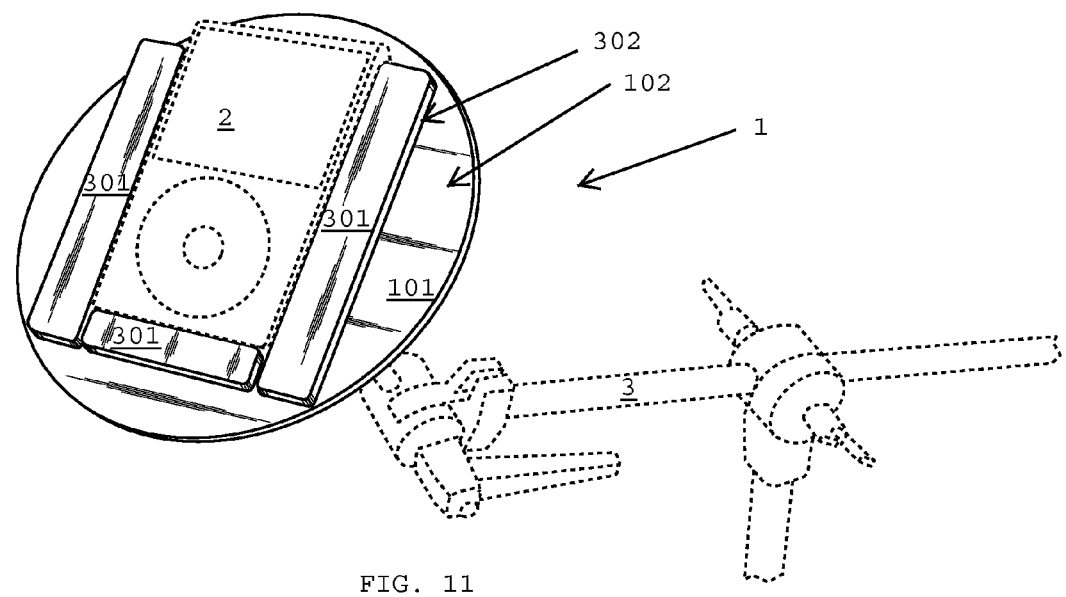
FIG. 11 is a perspective view of the apparatus 1 attached to a support 3.

FIG. 11 illustrates a contextual view of the apparatus 1 provided to a support 3. As depicted in the figure, a media/audio player 2 has been provided to a securing means 300 adapted to the size and shape of the player 2. Also seen in the figure is the support 3 to which the apparatus 1 is provided. In this particular embodiment, the support 3 is a stand-alone structure with multiple degrees of freedom for positioning the surface 101 of the platform 100 toward the musician and at a height whereby the media/audio player may be rapidly operated, placed, and removed. The apparatus 1 is provided to the support 3 via a screw and nut system operating through the aperture 203.

Figure 12:
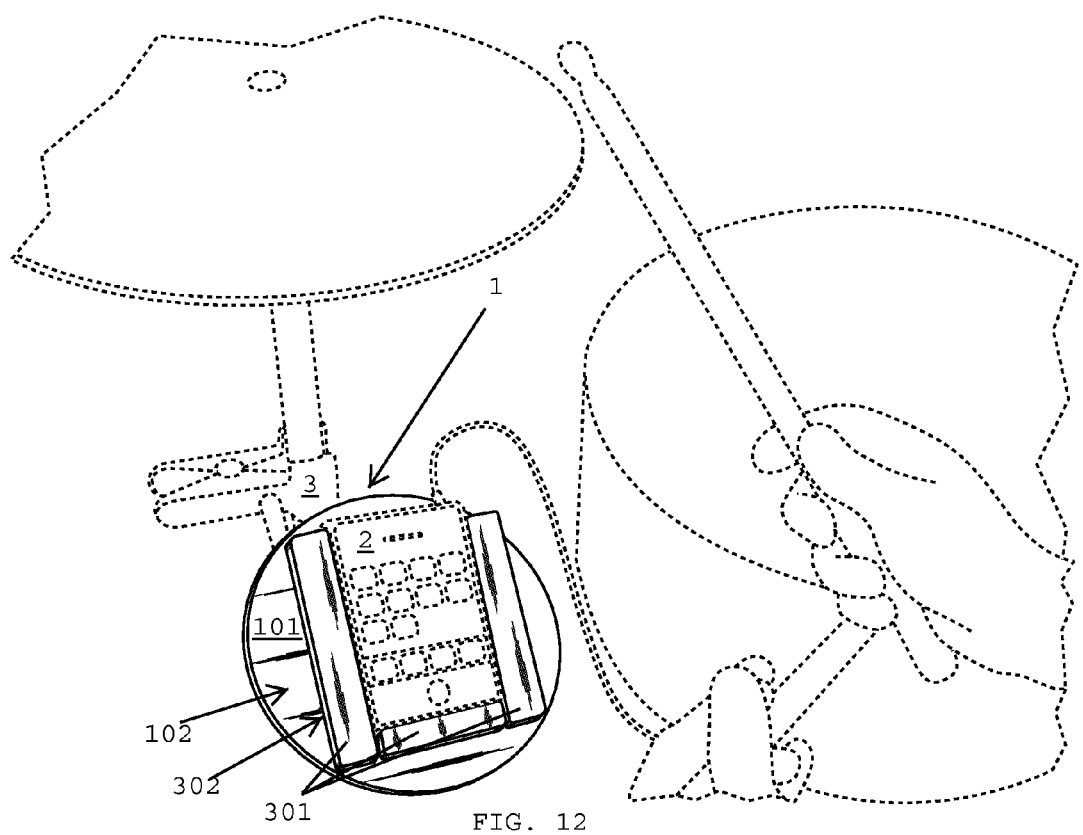
FIG. 12 is a contextual view of the apparatus 1 attached to a drum kit.
Figure 13A:
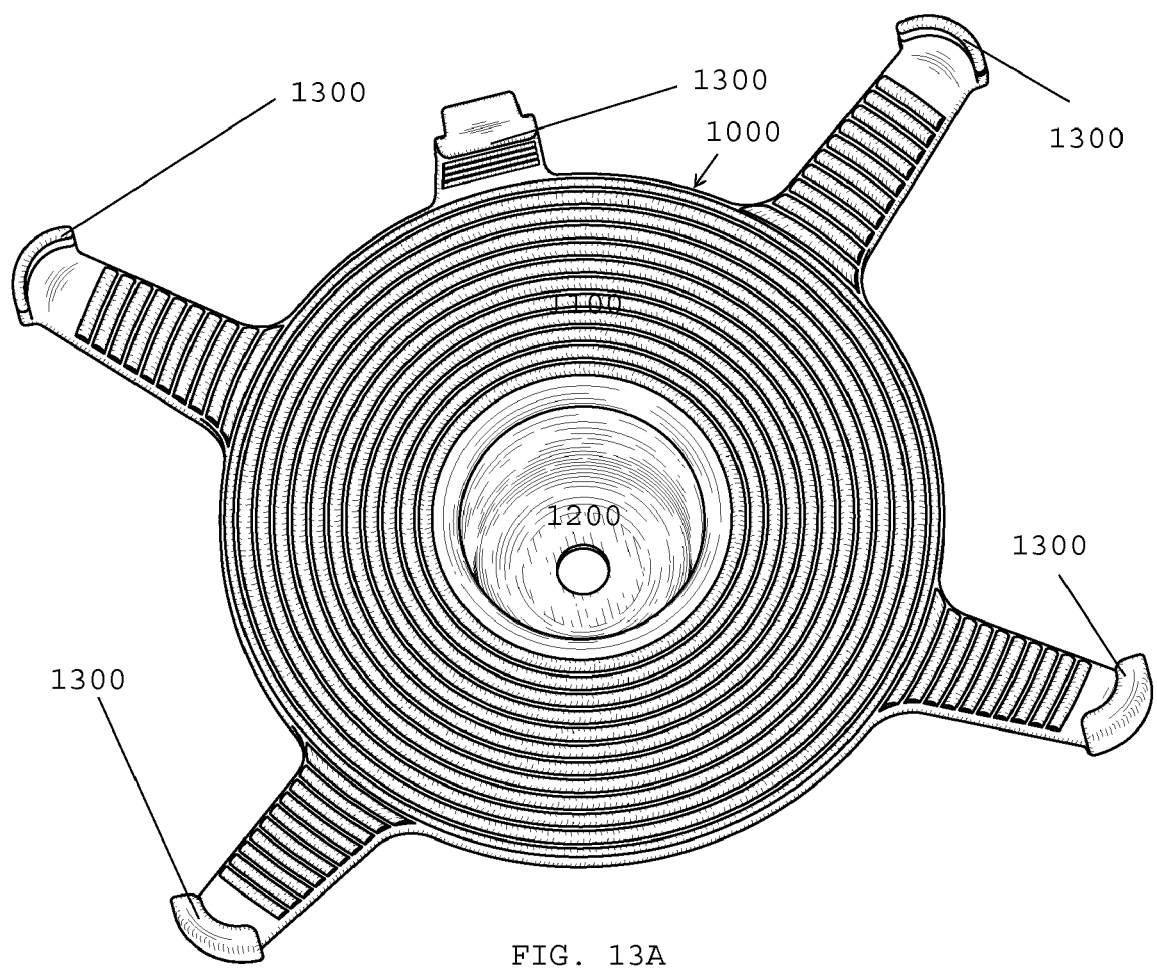
FIG. 13A is a perspective view of another apparatus 1000 of the present application.
Figure 13B:
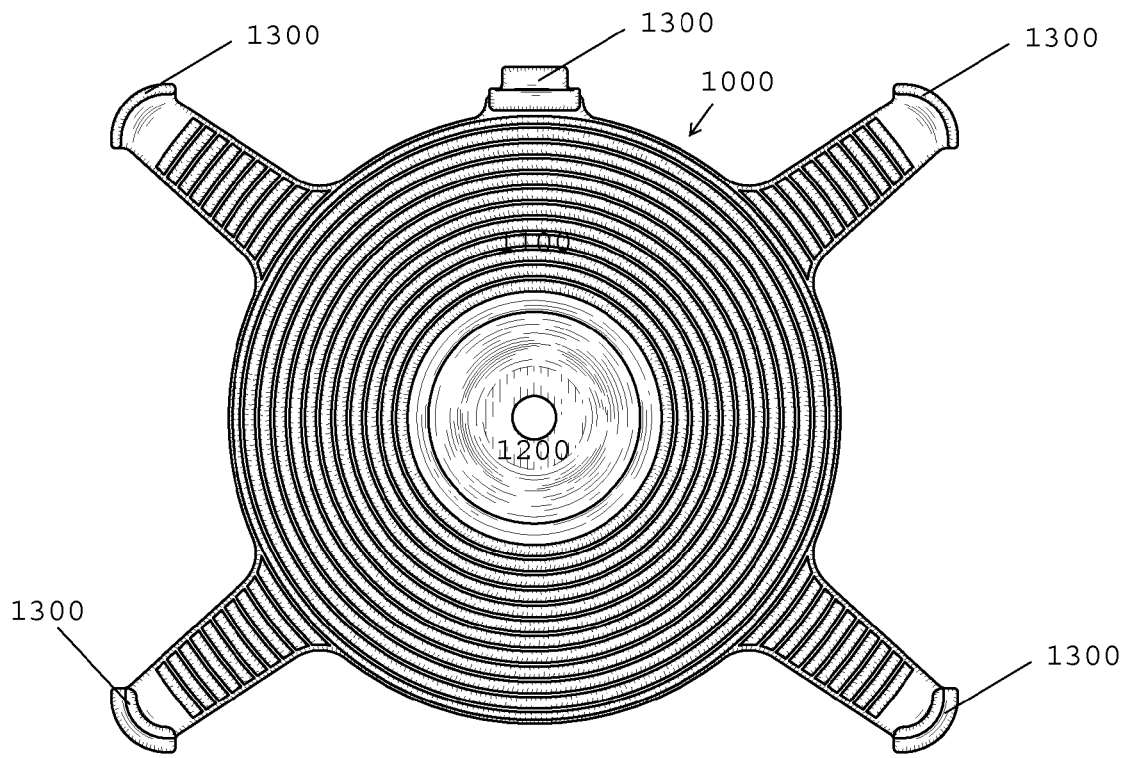
FIG. 13B is a front plan view of the apparatus 1000 of FIG. 13A.
Figure 13C:
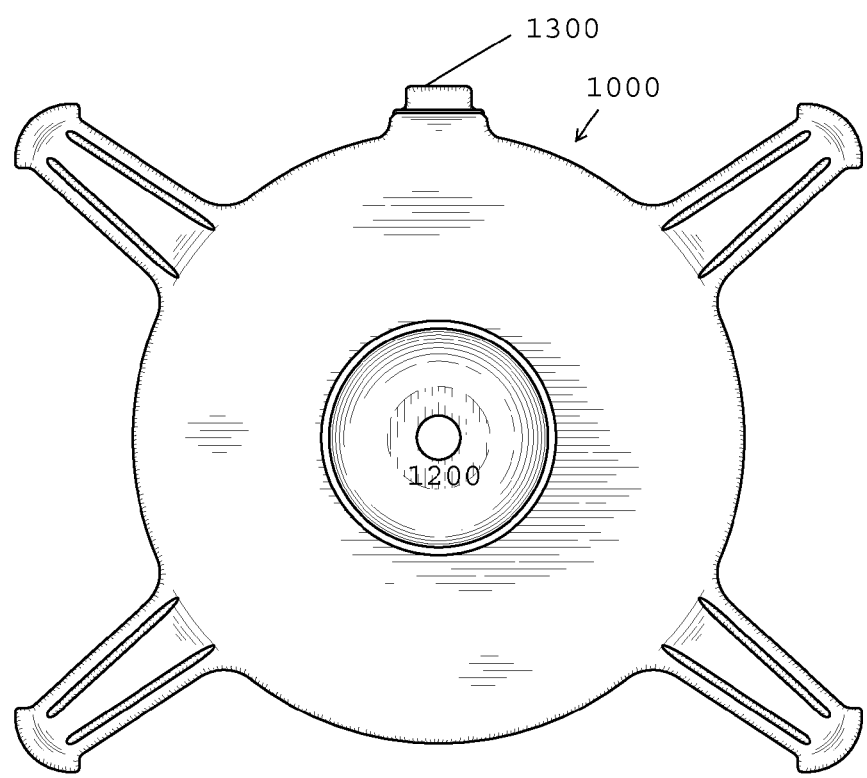
FIG. 13C is a back plan view of the apparatus 1000 of FIG. 13A.
Figure 13D:
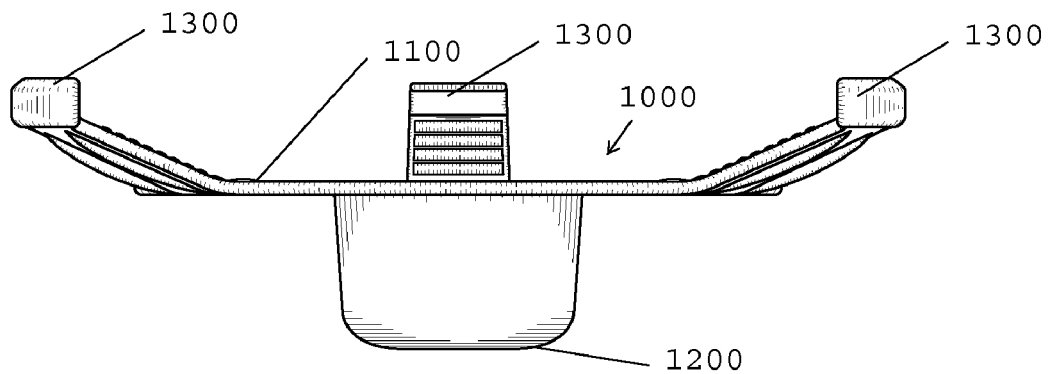
FIG. 13D is a top plan view of the apparatus 1000 of FIG. 13A.
Figure 13E:
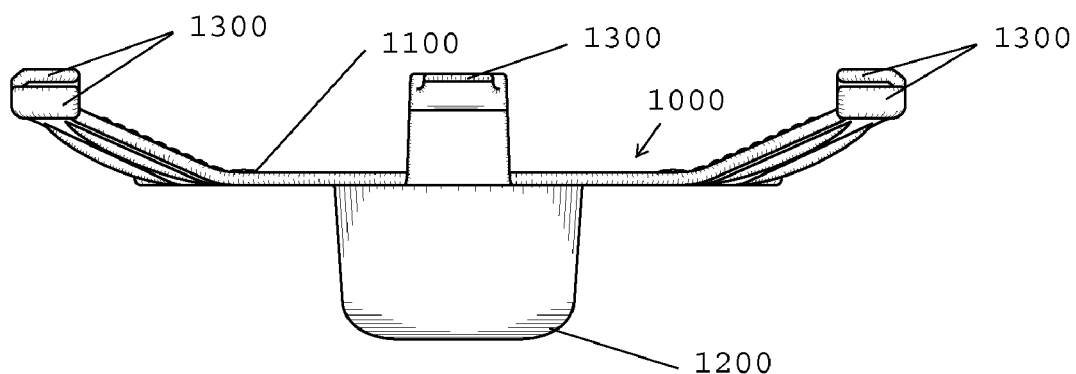
FIG. 13E is a bottom plan view of the apparatus 1000 of FIG. 13A.
Figure 13F:
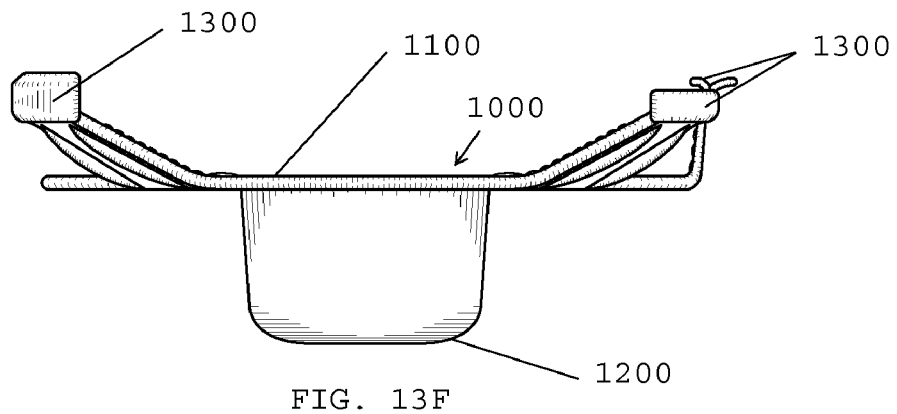
FIG. 13F is a right side plan view of the apparatus 1000 of FIG. 13A.
Figure 13G:
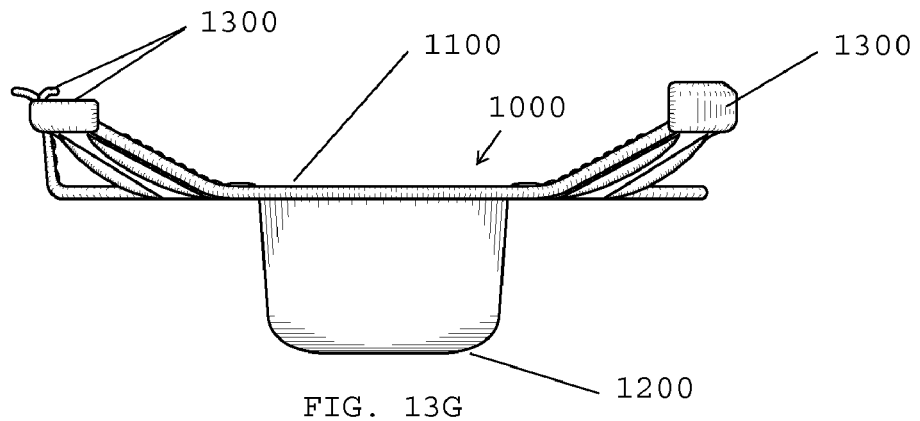
FIG. 13G is a left side plan view of the apparatus 1000 of FIG. 13A.
Figure 13H:
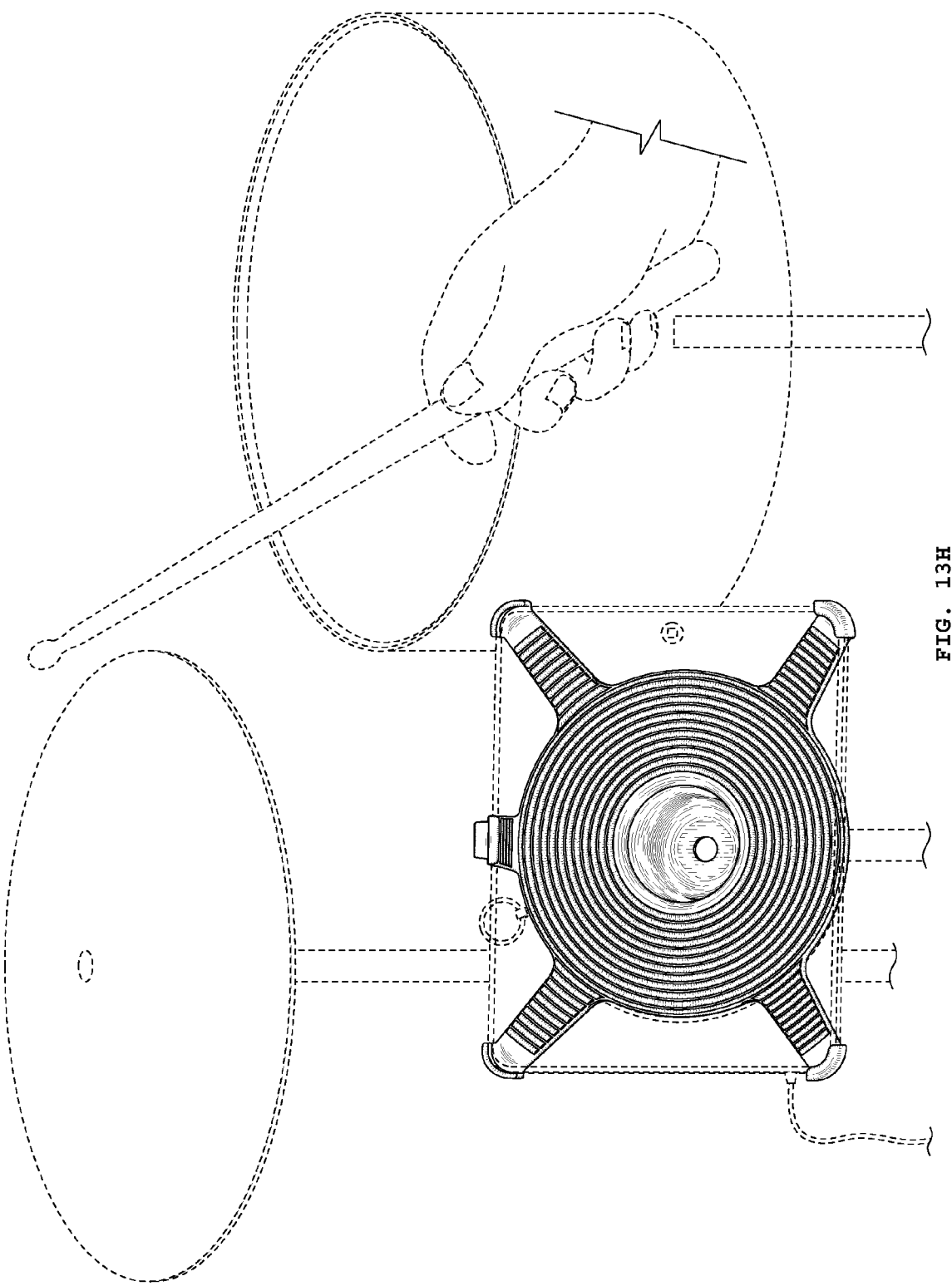
FIG. 13H is an environmental view of the apparatus 1000 of FIG. 13A.

FIG. 12 illustrates a contextual view of the apparatus 1 provided to a drum kit 4. As depicted in the figure, a media/audio player 2 has been provided to a securing means 300 adapted to the size and shape of the provided player 2. Also seen in the figure is the support 3 to which the apparatus 1 is provided. In this particular embodiment, the support 3 is coupled to a cymbal stand and the surface 101 of the platform 100 is directed toward a drummer at a height whereby the media/audio player may be rapidly operated, placed, and removed while the drummer is playing the associated drum kit. The apparatus 1 is provided to the support 3 via a screw and nut system operating through the aperture 203.

It should be noted that the apparatus 1 may take on the general appearance of a cymbal in order to visually blend with the drum kit. Furthermore, the apparatus 1 may be mounted to a drum kit in a manner similar to a cymbal or on a cymbal stand. The stated features assist the drummer in maintaining fluency during drumming because the drummer will not likely be distracted by an apparently foreign object.

FIG. 13A-13H are respectively a perspective view, a front view, a back view, a top view, a bottom view, a right side view, a left side view, and an environmental view of another apparatus 1000. As seen in these figures, the apparatus 1000 typically comprises three main features: (1) a support platform 1100; (2) a base 1200; and (3) a means for securing a particular media/audio player 1300 to the apparatus 1000. The disclosed apparatus 1000 operates generally in the manner disclosed above in connection with the apparatus 1 (depicted in FIGS. 1-12) and its securing means 1300 are suitably positioned on the support surface 1100 to accommodate media/audio players of the tablet computer variety (e.g., iPad (trademark of Apple, Inc.). The support platform 1100 generally operates like, and has similar components as, the support platform 100 of the apparatus 1 (depicted in FIGS. 1-12), except that the platform 1100 is made larger to accommodate media/audio players of the tablet variety via extensions 1110. The base 1200 generally operates like, and has similar components as, the base 200 of the apparatus 1 (depicted in FIGS. 1-12). The securing means 1300 generally operate like, and have similar components as, the securing means 300 of the apparatus 1 (depicted in FIGS. 1-12). In the depicted embodiment, the securing means 1300 are affixedly positioned thereon the support platform to accommodate the dimensions of a media/audio player of the tablet variety rather than being adhered thereto in said configuration via an adhering means.

In summary, what is disclosed may be a method of accompanying a musical instrument comprising the steps of: obtaining a media/audio player 2; obtaining an apparatus 1 featuring a securing means 300; obtaining a support; attaching the apparatus 1 to said support; manipulating the securing means 300 to the size and dimensions of said media/audio player; placing said media/audio player within the apparatus 1; and moving said apparatus 1 and media player 2 within the operable reach of a musician; and operating the media/audio player 2. What is disclosed may also be an apparatus 1 comprising a base, support platform, and a securing means. What is disclosed may also be a method of setting-up a support apparatus comprising the steps of: obtaining an apparatus 1 featuring a securing means 300; obtaining a support; attaching the apparatus 1 to said support; manipulating the securing means 300 to the size and dimensions of a media/audio player; and moving said apparatus 1 to within the operable reach of a musician.

It should be noted that the figures and the associated descriptions are of illustrative importance only. In other words, the depictions and descriptions of the present invention should not be construed as limiting of the subject matter in this application. The apparatuses, assemblies, components, order and inclusion of steps, and methods discussed hereby are susceptible to modification without changing the overall concept of the disclosed invention. Such modifications might become apparent to one skilled in the art after reading this disclosure.

I claim:

1. A method of accompanying a musical instrument comprising the steps of:
    obtaining a media/audio player;
    obtaining an apparatus for holding a media/audio player and at least one securing means defined by at least one block—a structure element assuming a volume and having generally flat sides;
    wherein the apparatus comprises a base with an aperture and a platform extending from around the base to result in a surface to receive said player;
    obtaining a support for suspending the apparatus within a musical performance area;
    attaching the apparatus to said support via a connector operating through said aperture;
    positioning the securing means in an arrangement on said apparatus surface according to the size and dimensions of said player and so that an edge of said at least one block is oriented transverse relative to the surface; and
    placing said player either adjacent to a singular block or within the positioned securing means arrangement when plural blocks provide the securing means;
    moving said apparatus, support, and player within the operable reach of an instrument-playing musician; and,
    operating the player.

2. The method of claim 1 wherein the apparatus resembles a cymbal in size and shape, and said support is a cymbal stand of a drum kit.

3. The method of claim 1 wherein the step of positioning the securing means on said apparatus according to the size and dimensions of said player is facilitated via an adhering means.

4. The method of claim 1 wherein the securing means are defined by a plurality of block support structures.

5. The method of claim 3 wherein the securing means are defined by a plurality of block support structures, which may also be rectangular.

6. An apparatus for supporting a media/audio player, said apparatus comprising:
    a base, with a bottom that has an aperture configured for attachment to a support;
    a platform which extends around the base to form a surface; and
    securing means defined by four arms that are fixedly attached around the surface so that the arms extend outwardly from said platform, and wherein an edge of each arm is on an outward end of each structure, the four arm edges receiving a respective one corner of a media/audio player to secure the player to the platform.

7. The apparatus of claim 6 wherein said securing means are positioned on said surface of said platform according to the size and dimensions of said player.

8. The apparatus of claim 6 wherein the support is defined by a musical instrument structure.

9. The apparatus of claim 8 wherein the apparatus resembles a cymbal, and said support is a cymbal stand of a drum kit.

10. The apparatus of claim 9 wherein the base is configured for attachment to the cymbal stand via a connector operating through the aperture.

11. The apparatus of claim 10 wherein the apparatus resembles a cymbal in view of said platform extending around said base to form a disk.

12. A method of setting-up a support platform comprising the steps of:
    obtaining an apparatus featuring the support platform positioned around a base with an aperture;
    arranging at least one securing means on the platform defined by at least one block—a structure element assuming a volume and having generally flat sides, and wherein an edge of said at least one block is configured for abutment with a media/audio player to secure it in place;
    obtaining a support for suspending the platform at a location preferred by an instrument-playing musician;
    attaching the apparatus to said support by operating a connector through the aperture in the base of the apparatus;
    ensuring that said edge of the securing means is positioned according to the size and dimensions of the media/audio player; and
    moving said apparatus to within the operable reach of an instrument-playing musician into a preferred position.

13. The method of claim 12 wherein the support platform resembles a cymbal in size and shape, and said support is a cymbal stand of a drum kit.

14. The method of claim 12 wherein the step of ensuring that, relative to said support platform, said edge, of the securing means is positioned according to the size and dimensions of said player is accomplished via a hook and loop adhering system between said support structures and said platform.

15. The method of claim 12 wherein the securing means are defined by a plurality of rectangular block support structures.

16. The method of claim 13 wherein the securing means are defined by at least one support structure in the general form of a rectangular block.

17. The apparatus of claim 14 wherein the securing means are defined by a plurality of thin blocks.

* * * * *